(12) United States Patent
Feng

(10) Patent No.: US 8,828,202 B2
(45) Date of Patent: Sep. 9, 2014

(54) DETACHABLE DISSOLVED OXYGEN SENSOR FOR SINGLE USE BIOREACTOR/MIXER

(75) Inventor: Chang-Dong Feng, Long Beach, CA (US)

(73) Assignee: Rosemount Analytical Inc., Irvine, CA (US)

(*) Notice: Subject to any disclaimer, the term of this patent is extended or adjusted under 35 U.S.C. 154(b) by 0 days.

(21) Appl. No.: 13/325,260

(22) Filed: Dec. 14, 2011

(65) Prior Publication Data

US 2012/0160677 A1 Jun. 28, 2012

Related U.S. Application Data

(60) Provisional application No. 61/424,261, filed on Dec. 17, 2010.

(51) Int. Cl.
*G01N 27/416* (2006.01)
*G01N 27/327* (2006.01)
*G01N 27/404* (2006.01)
*C12M 1/34* (2006.01)

(52) U.S. Cl.
CPC .................. *G01N 27/404* (2013.01); *C12M 41/32* (2013.01)
USPC .................. 204/403.02; 204/403.06; 204/415

(58) Field of Classification Search
USPC ............ 204/403.01–403.15, 415, 416, 204/418–420, 433; 205/777.5, 778, 779, 205/782, 782.5, 783, 785.5, 787.5, 792–793
See application file for complete search history.

(56) References Cited

U.S. PATENT DOCUMENTS

| | | | | |
|---|---|---|---|---|
| 4,263,115 A | * | 4/1981 | Kessler et al. | 204/418 |
| 4,294,124 A | * | 10/1981 | Kalwaitis | 73/863.85 |
| 4,305,286 A | * | 12/1981 | Beuth et al. | 374/134 |
| 6,602,401 B1 | * | 8/2003 | Feng | 205/783 |
| 6,894,502 B2 | | 5/2005 | Feng et al. | 324/438 |
| 2001/0028865 A1 | * | 10/2001 | Cummings et al. | 422/103 |
| 2002/0072084 A1 | | 6/2002 | Meserol et al. | 435/26 |
| 2003/0168403 A1 | * | 9/2003 | Corcho-Sanchez et al. | 210/631 |
| 2004/0140211 A1 | * | 7/2004 | Broy et al. | 204/424 |

(Continued)

FOREIGN PATENT DOCUMENTS

| | | |
|---|---|---|
| EP | 0399227 | 11/1990 |
| EP | 0753737 | 1/1997 |

(Continued)

OTHER PUBLICATIONS

International Search Report and the Written Opinion from the correspondence International patent application No. PCT/US2011/0685032 dated Apr. 26, 2012.
International Search Report and the Written Opinion from the related International patent application No. PCT/US2011/065033 dated Mar. 19, 2012.
Pharmaceutical Industry Solutions: Reliable Liquid Analysis. Brochure by Rosemount Analytical. Emerson Process Management.

(Continued)

*Primary Examiner* — Susan D Leong
(74) *Attorney, Agent, or Firm* — Christopher R. Christenson; Kelly, Holt & Christenson, PLLC

(57) ABSTRACT

A dissolved oxygen sensor for use with a single use-bioreactor/container is provided. The bioreaction vessel includes a plastic wall defining a bioreaction chamber therein, and having an aperture therethrough. A membrane holder is attached to an inner surface of the plastic wall. The membrane holder has a cylindrical portion passing through the aperture. A sensor window membrane is coupled to the membrane holder proximate the aperture. The sensor window membrane has a high oxygen permeability, but forms a water-tight seal with the membrane holder.

11 Claims, 5 Drawing Sheets

(56) References Cited

U.S. PATENT DOCUMENTS

| | | | |
|---|---|---|---|
| 2006/0228804 A1 | 10/2006 | Xu et al. | 436/84 |
| 2008/0032389 A1 | 2/2008 | Selker et al. | 435/283.1 |
| 2009/0130704 A1* | 5/2009 | Gyure | 435/41 |

FOREIGN PATENT DOCUMENTS

| | | |
|---|---|---|
| EP | 2065701 | 6/2009 |
| GB | 2364125 | 1/2001 |
| JP | 2008039523 | 2/2008 |
| WO | WO 92/01218 | 1/1992 |
| WO | WO 2009/017765 | 2/2009 |

OTHER PUBLICATIONS

S. Schmitmeier et al. "Development and Characterization of a Small-Scale Bioreactor Based on a Bioartificial Hepatic Culture Model for Predictive Pharmacological In Vitro Screenings", Biotechnology and Bioengineering, vol. 95, No. 6. Dec. 20, 2006.

Application Data Sheet. Tighter pH Control in Biopharmaceutical Applications. Jan. 2008 by Rosemount Analytical. Emerson Process Management.

Theory and Practice of pH Measurement. PN 44-6033/rev. D. Dec. 2010 by Rosemount Analytical. Emerson Process Management.

Related U.S. Appl. No. 13/325,254.

First Office Action from counterpart Chinese patent application No. 201210085580.X, issuing date Jun. 11, 2014. 14 pages.

* cited by examiner

DETACHABLE DISSOLVED OXYGEN SENSOR FOR SINGLE USE BIOREACTOR/MIXER

CROSS-REFERENCE TO RELATED APPLICATION

The present application is based on and claims the benefit of U.S. provisional patent applications Ser. No. 61/424,261, filed Dec. 17, 2010, the contents of which application is hereby incorporated by reference in its entirety.

BACKGROUND

Oxygen is a gas of significant interest, simply because of its role from the cycle of all living organisms. Measurement of oxygen concentration or partial pressure is important in the wide variety of the applications. In some applications, gaseous oxygen concentrations are measured directly. In other applications, the concentration of oxygen dissolved in a liquid is measured. It is important to realize that the term "dissolved oxygen" refers to gaseous oxygen dissolved in water, and it should not be confused with combined oxygen as found in the water molecule, $H_2O$.

A promising application for the measurement of dissolved oxygen is in biological specimens. These biological specimens may be in vitro specimens in a laboratory, or in vivo specimens within a patient. The measurement of dissolved oxygen in biological specimens provides important diagnostic information for care providers, and/or information about the efficacy of a particular treatment.

Frequently, a biological specimen is contained within a bioreactor/mixer, and the dissolved oxygen measurement provides important information about the state of the biomass contained therein.

SUMMARY

A dissolved oxygen sensor for use with a single use-bioreactor/container is provided. The bioreaction vessel includes a plastic wall defining a bioreaction chamber therein, and having an aperture therethrough. A membrane holder is attached to an inner surface of the plastic wall. The membrane holder has a cylindrical portion passing through the aperture. A sensor window membrane is coupled to the membrane holder proximate the aperture. The sensor window membrane has a high oxygen permeability, but forms a water-tight seal with the membrane holder.

DETAILED DESCRIPTION OF ILLUSTRATIVE EMBODIMENTS

Figure 1:
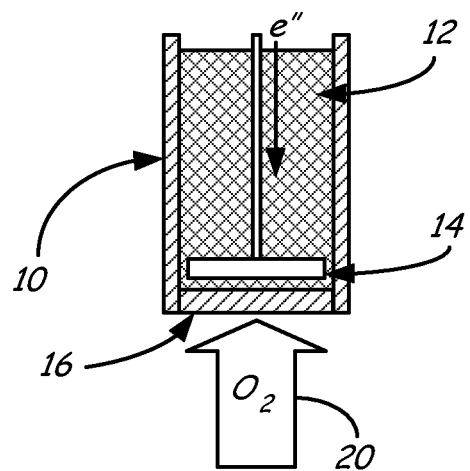
FIG. 1 is a diagrammatic view of an exemplary amperometric sensor with which embodiments of the present invention are particularly useful.

FIG. 1 is a diagrammatic view of an exemplary amperometric sensor with which embodiments of the present invention are particularly useful. Sensor 1 includes sensor body 10 and sensing membrane 16 that cooperate to provide a chamber within which supporting electrolyte 12 is maintained. Sensing electrode 14 is disposed within the chamber proximate sensing membrane 16. Sensor 1 is considered an amperometric dissolved oxygen sensor. Such sensors have been developed for many applications since the 1960s. The principal of the amperometric oxygen sensor is shown in FIG. 1. Specifically, sensing membrane 16 has a defined oxygen permeability, which controls the flow of oxygen molecules 20 diffusing through membrane 16. Once the oxygen molecule reaches the inner side of sensing membrane 16, it is reduced by sensing electrode 14 due to the electrode reaction (shown in FIG. 1) and generates a current signal. The magnitude of the current signal is proportional to the oxygen partial pressure at sensing membrane 16.

Figure 2:
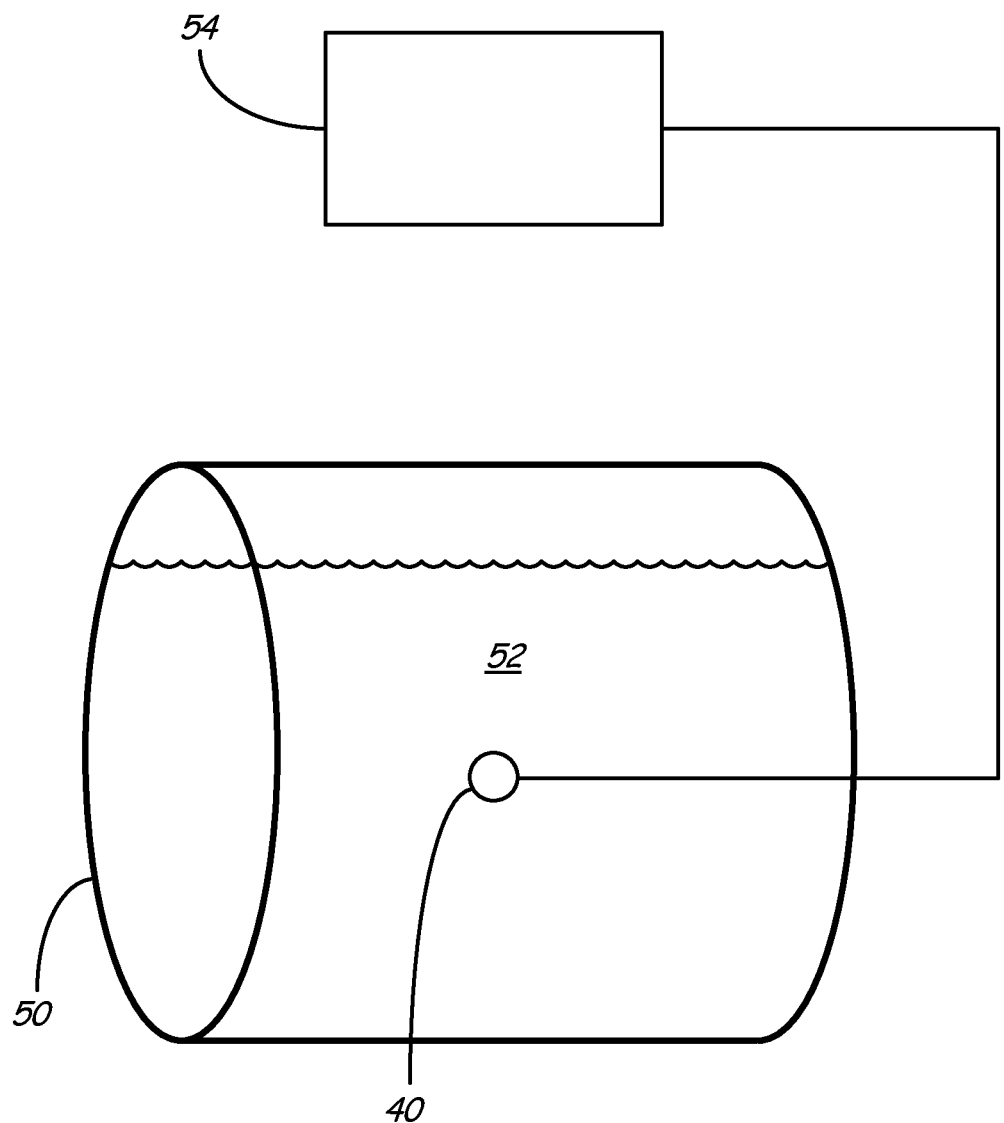
FIG. 2 is a diagrammatic view of an amperometric dissolved oxygen sensor being used to measure the dissolved oxygen content of a biological specimen within a single-use bioreactor in accordance with an embodiment of the present invention.

FIG. 2 is a diagrammatic view of an amperometric dissolved oxygen sensor being used to measure the dissolved oxygen content of a biological specimen within a single-use bioreactor in accordance with an embodiment of the present invention. Dissolved oxygen sensor 40 is mounted within single-use bioreactor 50 and disposed to provide an amperometric indication of the dissolved oxygen content of specimen 52. Sensor 40 is coupled to dissolved oxygen analyzer 54 which operates sensor 40. Analyzer 54 measures dissolved oxygen of specimen 52 using sensor 40 and provides a readout or other suitable indication of the dissolved oxygen content of specimen 52.

A design tension exists between the single-use nature of bioreactor 50 and traditional operation and insertion of a dissolved oxygen sensor in the bioreactor. In accordance with embodiments of the present invention, a dissolved oxygen sensor need not be in direct physical contact with the media within the single-use bioreactor. In this manner, the dissolved oxygen sensor can be inserted or removed without requiring sterilization processes.

Figure 3:
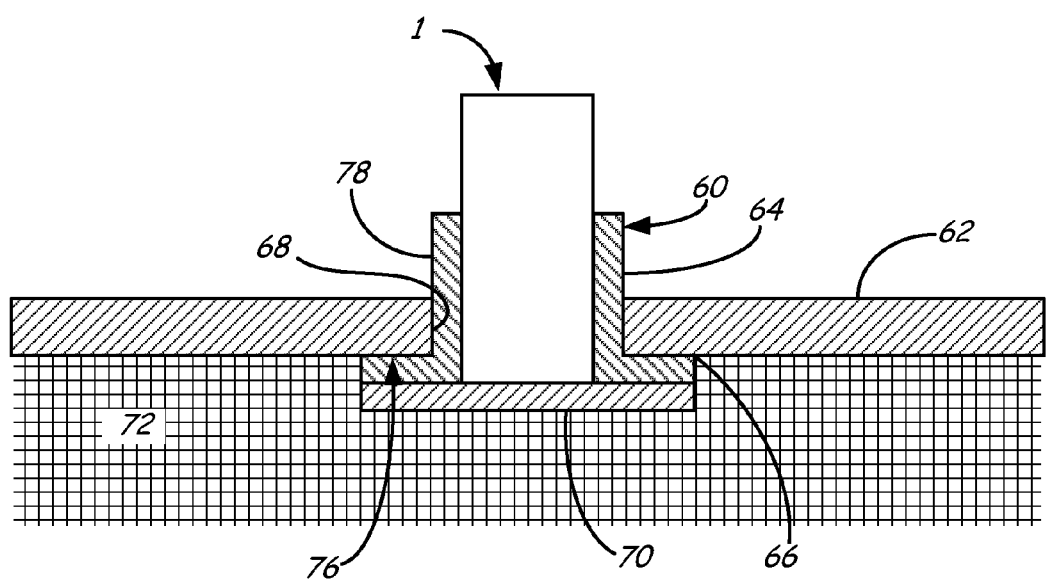
FIG. 3 is a diagrammatic view of the conventional dissolved oxygen sensor being employed to measure dissolved oxygen of a biological specimen in accordance with an embodiment of the present invention.

FIG. 3 is a diagrammatic view of the conventional dissolved oxygen sensor being employed to measure dissolved oxygen of a test medium or biological specimen in accordance with an embodiment of the present invention. Dissolved oxygen sensor 1 can be any suitable dissolved oxygen sensor, including that described above with respect to FIG. 1. Sensor 1 is mounted or otherwise affixed within sensor window holder 60. Sensor window holder 60 is welded, bonded, or otherwise mechanically affixed to wall 62 of bioreactor/mixer 50. An aperture 68 is formed through wall 62, which has a diameter that is approximately equal to the outside diameter of portion 64 of sensor window holder 60. Sensor window holder 60 is welded, bonded, or otherwise mechanically affixed to wall 62 at interface 66 and/or the interface between aperture 68 and outside diameter 64. Conventional dissolved oxygen sensor 1 can be removed from and reinstalled to sensor window holders 60 of various single-use bioreactors. Sensor window holder 60 also includes sensor window 70 disposed to contact the test media or biological specimen 72 and to preferably provide high permeation of oxygen. When the sensing membrane of a traditional oxygen sensor comes in contact with the sensing window 70, it will be able to measure the oxygen content of the media passing through the window 70. In one embodiment, sensor window membrane 70 is made from the material that has a high permeation of oxygen. Preferably, the oxygen permeability of sensor window membrane 70 is defined such that membrane 70 will generate at least 20 microamperes (μA) in air at sea level at 25° C. when installed on an amperometric sensor with a sensing electrode of 0.275 inches in diameter. The current defines the oxygen flows going through the membrane at this condition. The embodiment illustrated with respect to FIG. 3 allows the separation of dissolved oxygen sensor 1 and container 50 when required. Sensor 1 can simply be removed away from container 50 during steam sterilization or gamma irradiation of container 50. Moreover, sensor 1 can be removed from container 50 for calibration at any time without interrupting the process inside container 50.

Figure 4:
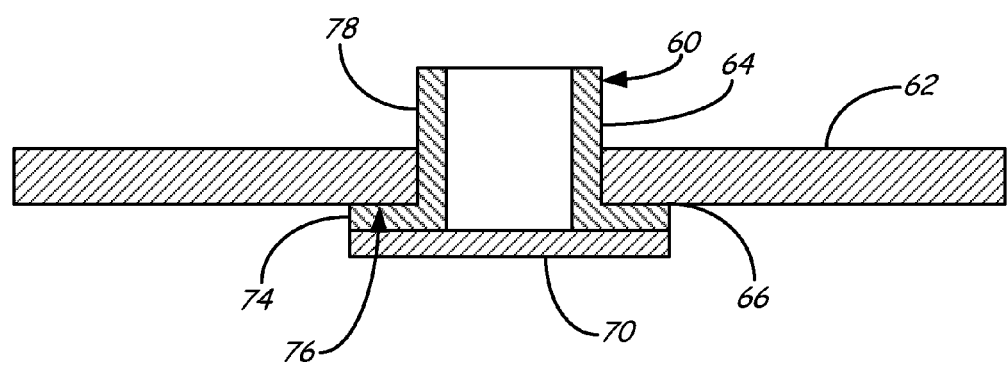
FIG. 4 is a diagrammatic cross-sectional view of a sensor window holder coupled to a wall or plastic sheet of a single-use bioreactor/mixer in accordance with an embodiment of the present invention.

FIG. 4 is a diagrammatic cross-sectional view of sensor window holder 60 coupled to a wall 62 or plastic sheet of a single-use bioreactor/mixer 50, in accordance with an embodiment of the present invention. Many aspects of the embodiment illustrated in FIG. 4 are similar to those illustrated in FIG. 3, and like components are numbered similarly. Specifically, plastic sheet or wall of container 62 is provided with an aperture that is roughly sized to pass the outside diameter 64 of cylindrical portion 78. Cylindrical portion 78 is coupled to flange member 74 that provides a face 76 that is sealed to the inside portion of single-use bioreactor 50. Flange member 74 may be sealed by any suitable methods including thermal/adhesive bonding, mechanical methods, such as ultrasonic welding, or other suitable methods. Additionally, sensing membrane 70 is sealed to flange 74 such that a water-tight connection is formed. Specifically, when sensing membrane 70 is affixed to flange member 74, and flange member 74 is affixed to the inside surface of wall 62 of single-use bioreactor 5-, the test medium of biological specimen contained within the single-use bioreactor cannot leak out.

In FIG. 4, sensing membrane 70 is integrated into the single-use bioreactor through by virtue of being a component of membrane holder 60. Sensing membrane 70, membrane holder 60, and plastic sheet 62 of the bioreactor are all attached together by thermal/adhesive bonding or any other suitable mechanical means. Additionally, sensing membrane 70 can be modified for reinforcement. In this configuration, sensing membrane 70 can be sterilized together with the single-use bioreactor/container through gamma irradiation or other suitable means. During the use of the single-use bioreactor, the electrolyte and sensing electrode can be installed for oxygen measurement without extra sterilization processes as shown in FIG. 4.

Figure 5:
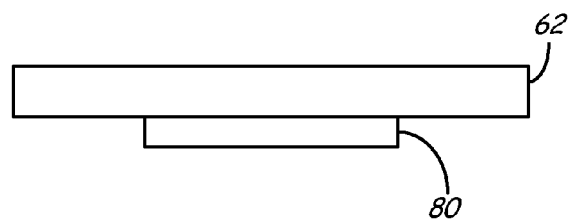
FIG. 5 is a diagrammatic view of a sensing membrane coupled to a wall of a single-use bioreactor mixer/container in accordance with an embodiment of the present invention.

In many embodiments, the sensing membrane will typically be made from polytetrafluoroethylene (PTFE) or a similar polymer with a relatively small permeability of oxygen. Most other polymers such as polypropylene or polyethylene have an oxygen permeability that is several orders of magnitude higher. In accordance with at least one embodiment of the present invention, the sensing membrane can be integrated into the single-use bioreactor by simply bonding the sensing membrane to the wall of the plastic sheet of the single-use bioreactor as illustrated diagrammatically in FIG. 5. In FIG. 5, the sensing membrane has a relatively lower oxygen permeability in comparison to the plastic sheet of the single-use bioreactor. One example of such a situation would be where the sensing membrane is constructed from polytetrafluoroethylene and the plastic sheet of the single-use bioreactor is constructed from polypropylene or polyethylene. The remainder of the sensor body and electrode can be disposed on either side of the plastic sheet or sensing membrane.

Figure 6:
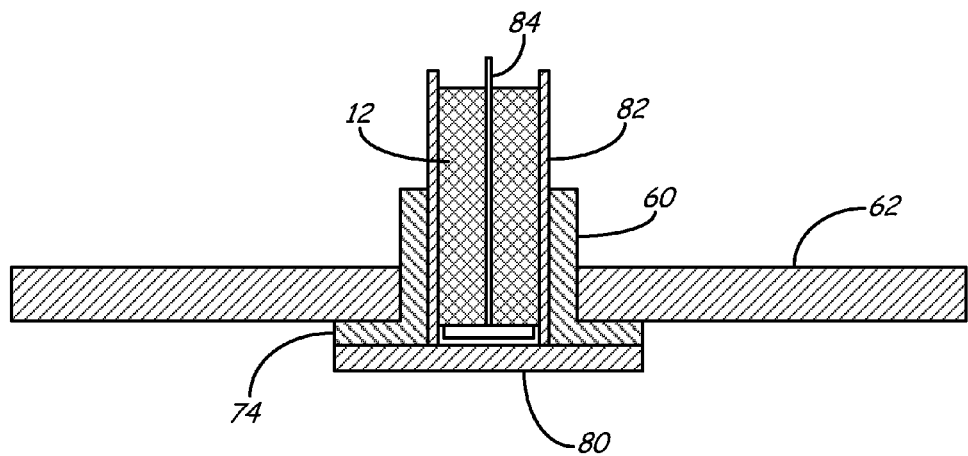
FIG. 6 is a diagrammatic view of a dissolved oxygen sensor coupled to a single-use bioreactor/mixer in accordance with an embodiment of the present invention.

FIG. 6 is a diagrammatic view of a dissolved oxygen sensor coupled to a single-use bioreactor/mixer in accordance with an embodiment of the present invention. The embodiment illustrated with respect to FIG. 6 is similar to that illustrated in FIG. 3, however the primary distinction is that sensing membrane 80 of the dissolved oxygen sensor illustrated in FIG. 6 is bonded, or otherwise adhered to the plastic wall of the single-use bioreactor through flange 74. In comparison, conventional dissolved oxygen sensor 1 illustrated in FIG. 3 has its own sensing membrane that abuts sensor window 70 such that oxygen permeates through sensor window 70 and the sensing membrane of the conventional dissolved oxygen sensor 1. As illustrated in FIG. 6, the oxygen merely passes through sensing membrane 80 and is substantially immediately reduced by the sensing electrode to generate a current signal. In this manner, the embodiment illustrated in FIG. 6 may react slightly quicker than embodiments that utilize a conventional dissolved oxygen sensor. Those skilled in the art will appreciate that sensor body 82 and electrode 84 do not comprise a complete dissolved oxygen sensor. Accordingly, in order to facilitate the embodiment illustrated with respect to FIG. 6, sensor body 82, electrode 84, and supporting electrolyte 12 are essentially provided as a kit that can be coupled to single-use bioreactors that contain, or otherwise employ membrane holder 60 and sensing membrane 80 as illustrated in FIG. 6. Thus, when a single-use bioreactor is ready to be employed, sensor body 82 is threaded, or otherwise detachably affixed to membrane holder 60 with electrode 84 therein. Once coupled, sensor body 82 and membrane holder 60 form a liquid-tight chamber with sensing membrane 80. Supporting electrolyte 12 is then introduced into the chamber to provide a fully-functional dissolved oxygen sensor. Once the reaction is complete, or otherwise terminated, sensor body 82 may be withdrawn from membrane holder 60 to be used with another single-use bioreactor, or sensor body 82 can be simply be removed from the same single-use bioreactor as that bioreactor is sterilized or otherwise subjected to gamma irradiation.

Although the present invention has been described with reference to preferred embodiments, workers skilled in the art will recognize that changes may be made in form and detail without departing from the spirit and scope of the invention.

What is claimed is:
1. A single-use bioreaction vessel comprising:
a plastic wall containing an aperture therethrough;
a membrane holder having a cylindrical portion and a flange portion affixed to the plastic wall, wherein the membrane holder is configured to removably mount an oxygen sensor external to the bioreaction vessel; and
a window membrane composed of a plastic having a high oxygen permeability and being coupled to the membrane holder to seal the aperture, the window membrane being disposed to contact a bioreaction material within the single-use bioreaction vessel and wherein the window membrane is configured to contact the oxygen sensor when the oxygen sensor is mounted in the membrane holder;
wherein the window membrane is located and sealed to the aperture of the bioreaction vessel; wherein the sensor body is configured to be removably coupleable such that the removal of the sensor body from the cylindrical portion does not breach the reaction vessel and the win- dow membrane remains attached to the bioreaction vessel even after removal of the sensor body.

2. The bioreaction vessel of claim 1, and further comprising a sensor body coupled to the cylindrical portion.

3. The bioreaction vessel of claim 2, and further comprising a sensing membrane disposed proximate the window membrane.

4. The bioreaction vessel of claim 3, and further comprising an analyzer operably coupled to the electrode to measure dissolved oxygen in a biological specimen based on current flow through the electrode.

5. A bioreaction vessel comprising:
   a plastic wall defining a bioreaction chamber therein, and having an aperture therethrough;
   a membrane holder attached to the plastic wall, the membrane holder having a cylindrical portion passing through the aperture;
   a sensor window membrane coupled to the membrane holder proximate the aperture, the sensor window membrane being composed of a plastic having a high oxygen permeability, but forming a water-tight seal with the membrane holder; and
   a sensor mounted proximate the sensor window outside of the bioreaction vessel such that the sensor window membrane is a sensing membrane of the sensor and such that the sensor window and the sensor are in direct contact;
   wherein the window membrane is located and sealed to the aperture of the bioreaction vessel; wherein the sensor body is configured to be removably coupleable such that the removal of the sensor body from the cylindrical portion does not breach the reaction vessel and the window membrane remains attached to the bioreaction vessel even after removal of the sensor body.

6. The bioreaction vessel of claim 5, and further comprising an amperometric dissolved oxygen sensor disposed in the cylindrical portion of the membrane holder.

7. The bioreaction vessel of claim 6, wherein the amperometric dissolved oxygen sensor is threaded to the cylindrical portion.

8. The bioreaction vessel of claim 7, and further comprising an analyzer coupled to the dissolved oxygen sensor to measure dissolved oxygen of a biological specimen in the bioreaction vessel.

9. The bioreaction vessel of claim 1, wherein the oxygen sensor can be removed from the membrane holder without interrupting a process inside the bioreaction vessel.

10. The bioreaction vessel of claim 1, wherein the oxygen permeability of the window membrane is defined such that the window membrane generates at least 20 microamperes in air at sea level at 25° C. when installed on an amperometric sensor having a sensing electrode of 0.275 inches in diameter.

11. The bioreaction vessel of claim 1, and further including a dissolved oxygen sensor coupled to the cylindrical portion, wherein a sensing membrane of the dissolved oxygen sensor contacts the window membrane.

* * * * *